United States Patent
Tan

(10) Patent No.: US 6,174,282 B1
(45) Date of Patent: Jan. 16, 2001

(54) SPECULUM

(75) Inventor: Gary Gay Chee Tan, Osborne Park (AU)

(73) Assignee: MCA Medical Products PTY LTD, Osborne Park (AU)

( * ) Notice: Under 35 U.S.C. 154(b), the term of this patent shall be extended for 0 days.

(21) Appl. No.: 09/381,017

(22) PCT Filed: Sep. 9, 1998

(86) PCT No.: PCT/AU98/00737

§ 371 Date: Sep. 14, 1999

§ 102(e) Date: Sep. 14, 1999

(87) PCT Pub. No.: WO99/12466

PCT Pub. Date: Mar. 18, 1999

(30) Foreign Application Priority Data

Sep. 9, 1997 (AU) .................................................. PO 9067

(51) Int. Cl.[7] .............................................................. A61M 29/00
(52) U.S. Cl. ......................................................................... 600/224
(58) Field of Search ................................... 600/219, 220, 600/224

(56) References Cited

U.S. PATENT DOCUMENTS

| | | | |
|---|---|---|---|
| 52,014 | * | 1/1866 | Bartlett .................................. 600/224 |
| 380,745 | * | 4/1888 | Chamberlin ........................... 600/224 |
| 1,614,065 | * | 1/1927 | Guttmann .............................. 600/235 |
| 3,817,242 | | 6/1974 | Uddenberg . |
| 5,377,667 | * | 1/1995 | Patton et al. .......................... 600/220 |
| 5,916,151 | * | 6/1999 | Charters ................................ 600/224 |

FOREIGN PATENT DOCUMENTS

| | | |
|---|---|---|
| 2698778 | 6/1994 | (FR) . |
| 43218 | 1/1982 | (GB) . |
| 288157 | 10/1988 | (GB) . |
| WO 92/21279 | 12/1992 | (WO) . |
| WO 94/12091 | 6/1994 | (WO) . |

* cited by examiner

Primary Examiner—Gene Mancene
Assistant Examiner—Eduardo C. Robert
(74) Attorney, Agent, or Firm—Workman, Nydegger & Seeley

(57) ABSTRACT

A speculum (10) includes a main body (12) with two dilator fingers (14A and 14B) that are connected at their respective proximal ends (16A and 16B) to the main body (12). A further dilator finger (28) extends between the fingers (14A and 14B) and is fixed to the main body (12). An actuator (20) is pivotally coupled to the main body (12). The actuator (20) is formed with a dilator finger (70) that is located between the fingers (14A and 14B) and opposite the fixed finger (28). When the actuator (20) is pivoted the finger (70) immediately commences to pivot away from the remaining fingers (14) and (28). After a predetermined degree of pivot, the actuator (20) comes into contact with the inside of fingers (14) near their proximal ends (16) to cause the distal ends of those fingers to move away from each other. Fingers (14A and 14B) are hinged about respective canted hinge axis so that when they are abutted by the actuator (20) they move in a combined upward and sideways motion.

13 Claims, 4 Drawing Sheets

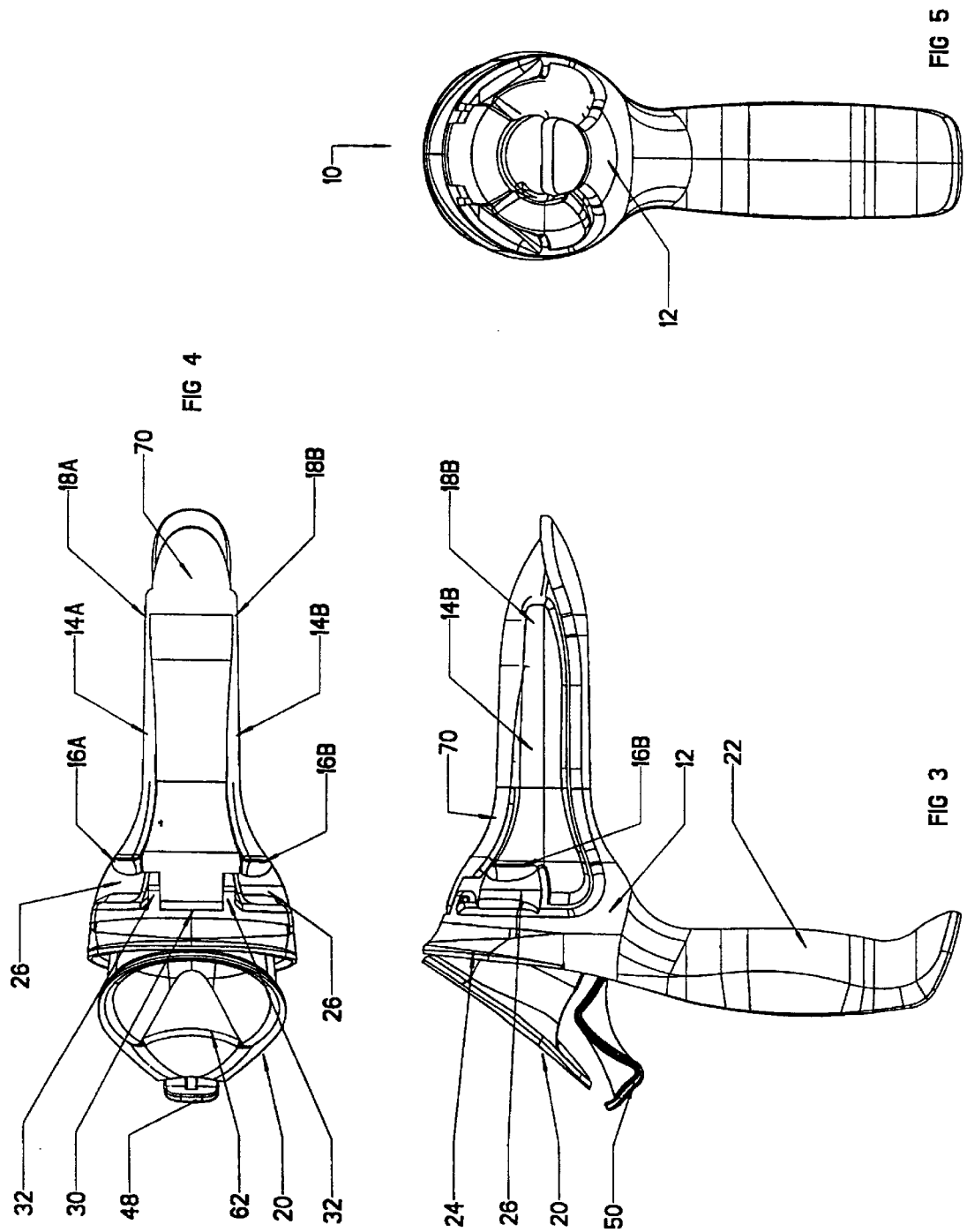

SPECULUM

FIELD OF THE INVENTION

This invention relates to a speculum for dilating, visualising and instrumenting a body cavity such as a vagina or rectum.

BACKGROUND TO THE INVENTION

A conventional speculum comprises a plurality of dilator members or arms which are spread by an actuator for enlarging a body cavity. There are commonly two types of actuators, the lever type and the cam or iris type. The lever type actuator typically comprises a pair of handles each having one dilator arm arranged in a manner so that when the handles are squeezed together the dilator arms spread apart. An inherent drawback with most lever type speculums is that the levers or handles are disposed in the line of sight of the body cavity therefore obscuring a view of the cavity under examination and/or interfering with the placement of medical instruments.

In the iris type speculums, the dilator arms are moved outwardly in a spiralling motion. As a result, the arms must slide against the tissue in the cavity being examined which may cause pinching of the tissue or discomfort to the patient. A further disadvantage with the known iris type speculums is their relatively complex construction and manufacture which increases costs to the extent that the speculums are in general, intended for multiple use. This therefore necessitates a strict hygiene and sterilisation program to ensure that there is no cross infection between patients. Accordingly, the use of iris type speculums is generally inconvenient to practitioners and increases the cost of service.

A further generation of speculums is known in which a rotating annular cam bears against the side of pivotal dilator arms causing the arms to pivot outwardly. An example of such a speculum is shown in Applicant's International application no. PCT/AU96/00125 (WO 96/28083). While this type of speculum has several advantages over the lever and iris type speculums described above, it is still relatively complex in manufacture requiring the production of numerous separate components which must then be assembled into the complete speculum.

SUMMARY OF THE INVENTION

It is an object of the present invention to provide a speculum which is inexpensive to manufacture and assemble and thus can be produced economically to facilitate once only disposable use and does not adversely affect visualisation or instrumenting of a body cavity.

According to the present invention there is provided a speculum for dilating a body cavity including:
a main body;
a plurality of first dilator fingers, coupled at their respective proximal ends to the main body in a manner to allow the respective distal ends of the first fingers to move away from each other; and,
an actuator pivotally coupled to the main body, the actuator provided with a second finger fixed thereto, wherein the actuator can be pivoted into abutment with the proximal ends of the first dilator fingers causing the distal ends of the first fingers and the second finger move away from each other thereby dilating the body cavity.

Preferably the actuator is arranged to pivot through a first angle prior to abutment with the first fingers so that the distal end of the second finger commences to move before the distal ends of the first fingers move.

Preferably the main body is provided with a third fixed finger which is located between adjacent ones of the first fingers and opposite the second finger.

Preferably the distal ends of the second and third fingers extend beyond the distal ends of the first fingers.

Preferably respective distal ends of first fingers are located inside the second and third fingers when the speculum is in a fully closed state.

Preferably the distal end of one of the second and third fingers extends beyond that of the other of the second and third fingers.

Preferably the first fingers are integrally formed with the main body and provided with respective integral hinges to allow movement away from each other.

Preferably each hinge has a hinge axis about which its corresponding finger can move, said hinge axis being canted so that the movement of the corresponding finger is a combined upward and sideways movement.

Preferably said main body comprises a first ring like structure to which said first dilator fingers are attached and said actuator comprises a second ring like structure which pivots inside said first ring like structure, said first and second ring like structures defining a window through which the cavity can be viewed when the distal ends of the fingers are moved away from each other.

Preferably said speculum further comprises a releasable locking mechanism for locking the relative positions of the fingers, and subsequently releasing the fingers.

Preferably said mechanism comprises a first component provided on said actuator and a second component provided on said main body, said first and second components arranged to engage each other when said actuator is pushed in the direction of insertion, and adapted to release from each other when force is applied to said actuator in a direction oblique to the direction of insertion.

Preferably said first component comprises one of a pawl and a rack of teeth like projections, and the second component comprises the other of the pawl and the rack, said pawl and rack being biased into engagement when the actuator is pushed in the direction of insertion, and being lifted apart to effect disengagement when said force is applied.

According to a second aspect of the present invention there is provided a speculum for dilating a body cavity including:
a main body;
a plurality of first dilator fingers coupled at their respective proximal ends to the main body in a manner to allow the respective distal ends of the first fingers to move away from each other; and
an actuator pivotally coupled to the main body, the actuator provided with a second finger fixed thereto, the second finger located between adjacent ones of the first fingers, the actuator arranged to abut the proximal ends of the first fingers when pivoted in a first direction, whereby when the speculum is in a fully closed state and actuator is pivoted in a first direction a distal end of the second fingers initially pivots away from the first fingers and when the actuator abuts the first fingers it causes their distal ends to move away from each other thereby dilating the body cavity.

According to a further aspect of the present invention there is provided a speculum for dilating a body cavity including:
a main body;
a plurality of first dilator fingers hinged at their proximal ends to the main body about respective canted hinge axes to allow the first dilator fingers to move with a combined upward and sideways motion; and an actuator pivotally coupled to the main body, the actuator provided with a second finger fixed thereto so that the actuator can be pivoted into abutment with the first dilator fingers causing the first fingers to move outwardly with said combined upward and sideways motion and the second finger to move away from the first fingers thereby dilating the body cavity.

BRIEF DESCRIPTION OF THE DRAWINGS

An embodiment of the present invention will now be described by way of example only, with reference to the accompanying drawings in which:

FIG. 3 is a side view of the speculum:

FIG. 4 is a top view of the speculum;

FIG. 5 is a front end view of the speculum;

DETAILED DESCRIPTION OF THE PREFERRED EMBODIMENT

Figure 2:
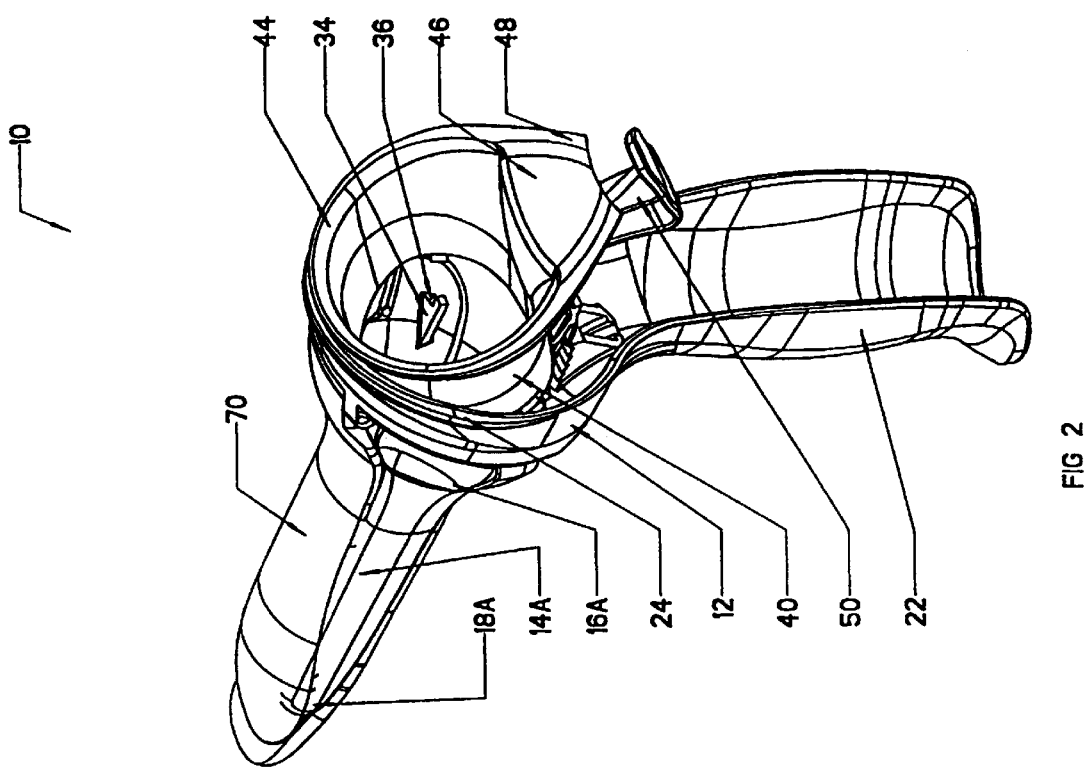
FIG. 2 is a perspective view of the speculum shown in FIG. 1 from the rear.

The speculum 10 comprises a main body 12 and a plurality (in this instance two) first dilator fingers 14A and 14B (hereinafter referred to collectively as "fingers 14"), which are each connected at their respective proximal ends 16A and 16B to the main body 12. The coupling of the fingers 14 to the main body 12 is in a manner so that the fingers 14 and in particular their respective distal ends 18A and 18B can move away from each other when acted upon by actuator 20. The actuator 20 is pivotally coupled to the main body 12 so that when it is pushed in a direction of insertion of the speculum into the body cavity, the actuator pivots into abutment with the inside of the fingers 14 near their proximal ends 16 causing the distal ends 18 to move away from each other thereby dilating the body cavity.

Figure 1:
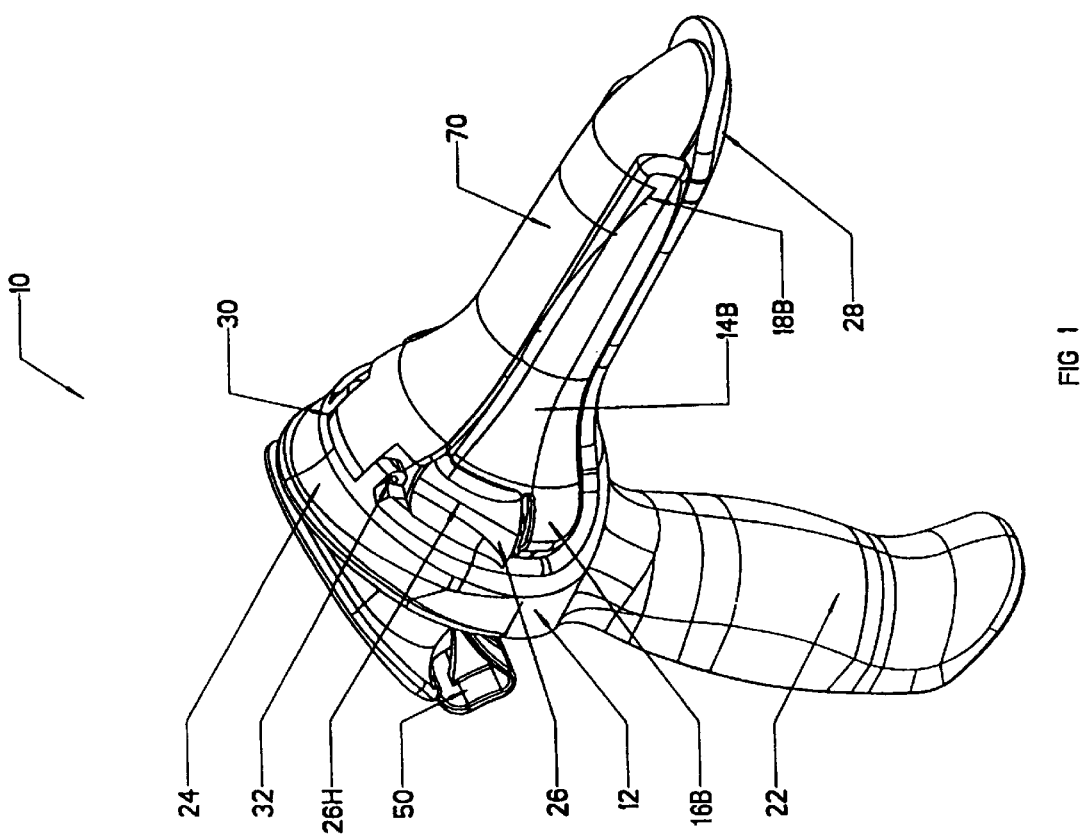
FIG. 1 is a perspective view from the front of a speculum in accordance with a first embodiment of the present invention.

The body 12 comprises a handle 22 which terminates at its upper end with a ring or annulus type structure 24. The fingers 14 are coupled to the structure 24 and extend in the axial direction of the structure 24 and generally perpendicularly to the handle 22. The fingers 14 are attached to the structure 24 by tabs which form hinges 26. Located between the lower longitudinal edges of fingers 14A and 14B is a further finger 28. The finger 28 is fixed to the ring like structure 24 and extends parallel to and beyond fingers 14. The main body 12, that is the handle 22, ring like structure 24, hinges 26 and fingers 14 and 28 are integrally formed as a single unit. As is evident from FIG. 1, each hinge 26 has a hinge axis 26H which is canted or inclined relative to its respective fingers 14 so that when fingers 14 move they move with a combined upwards and sideways motion. That is the hinge axis 26H about which a finger 14 moves extends along a tangent to ring like structure 24 but is inclined from the perpendicular to the longitudinal axis of that finger 14.

A rectangular cut-out 30 is formed on an upper part of the structure 24 between the fingers 14A and 14B. On each side of the cut-out 30 is an integrally formed detent 32. The detents 32 capture respective pins (not shown) formed on the actuator 20 to provide a snap-fit pivotal connection between the actuator 20 and the main body 12. The detents can be in the form of holes formed in lobes provided on opposite sides of the cut-out 30 for receiving the pins on the actuator 20.

A short rib 34 (see FIG. 2) is formed on the inside surface of each finger 14 adjacent its proximal end 16. The rib 34 extends in the direction of the length of its respective finger 14 and is provided at an end adjacent the ring structure 24 with a recess 36 at its proximal end. Each rib 34 is offset from the hinge 26 of its corresponding finger 14. Moreover, the hinge 26 and rib 34 of each finger 14 are spaced on opposite sides of longitudinal axis 38 of each finger 14, as seen most clearly in FIG. 6.

The actuator 20 also includes a ring like structure or shell 40 having an arcuate forward edge 42 and a rearward edge 44 which is also arcuate but inclined to the forward edge 42 so that the depth of the shell 40 generally increases from its top to its bottom. Extending rearwardly and downwardly from the bottom of the shell 40 is a thumb rest 46. The thumb rest 46 is in the form of a concave depression formed in a downwardly depending flange 48 integrally provided on the actuator 20.

Figure 6:
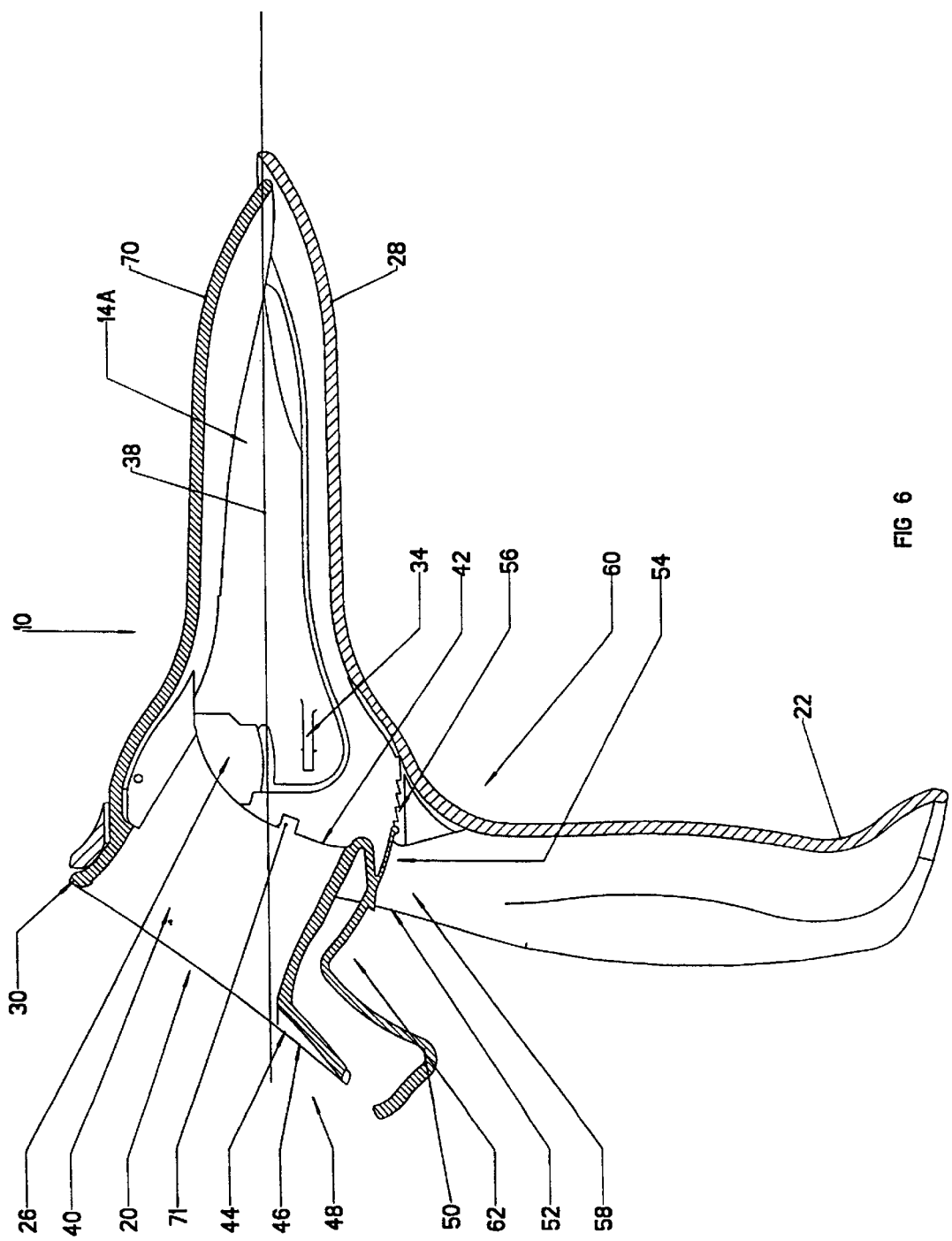
FIG. 6 is a sectional view of the speculum.

As best seen in FIG. 6, a releasable locking mechanism 52 is provided for locking the relative positions of the fingers so as to maintain a desired dilation of the body cavity and then allowing subsequent release of the fingers. The locking mechanism 52 comprises a first component in the form of a pawl 54 which is integrally formed with the actuator 20 and a rack 56 of teeth like projections formed on the inside of the ring like structure 24 and extending centrally along a length of the finger 28. The pawl 54 is part of a spring like thumb actuated release mechanism 50 that is integrally formed with forward edge 42 of the actuator 20 and extends rearwardly to a location adjacent the rearward edge 44.

The pawl 54 includes a tongue 58 that extends in the forward direction and disposed above the rack 56. The tongue 58 is biased so as to normally press on the rack 56. The forward most and rearward most ends of the tongue 58 are provided with a first barb 60 and second barb 62 respectively for engaging the rack 56. The barbs 60 and 62 are spaced so that the second barb 62 does not engage the rack 56 until the first barb has been pushed forward beyond the rack 56. Ideally the second barb 62 engages the rack 56 when the speculum is approximately half fully open. In this embodiment this corresponds roughly to the actuator 20 commencing to push against the inside of fingers 14. The shape and location of the second barb 62 provided for a greater bias against the rack 56 than the first barb 60.

The shape of the pawl 54, in combination with a nature of the material from which it is made and the juxtaposition of the actuator 20 to the main body 12 ensures that at all times at least one of the barbs 60, 62 are maintained in bias contact with the rack 56 when the actuator 20 is pivoted inwardly to spread the fingers of the speculum 10.

The purpose of the first barb 60 is mainly to provide tactile feed back to the user rather than to firmly hold the fingers in position. It is the second barb 62 that enables the distal ends of the fingers to be held apart with incrementally increasing spread as it engages successive teeth along the rack 56.

To release the fingers, the release mechanism 50 is pushed upwardly. This lifts the second barb 62 out of engagement with the rack 56. By now also pushing backwardly the actuator can be pivoted back in a controlled manner to close the speculum 10. The first barb 60 can still lightly engage the rack 56 however its engagement force is easily overcome by the upward and backward thumb pressure applied to the mechanism 50.

Figure 7:
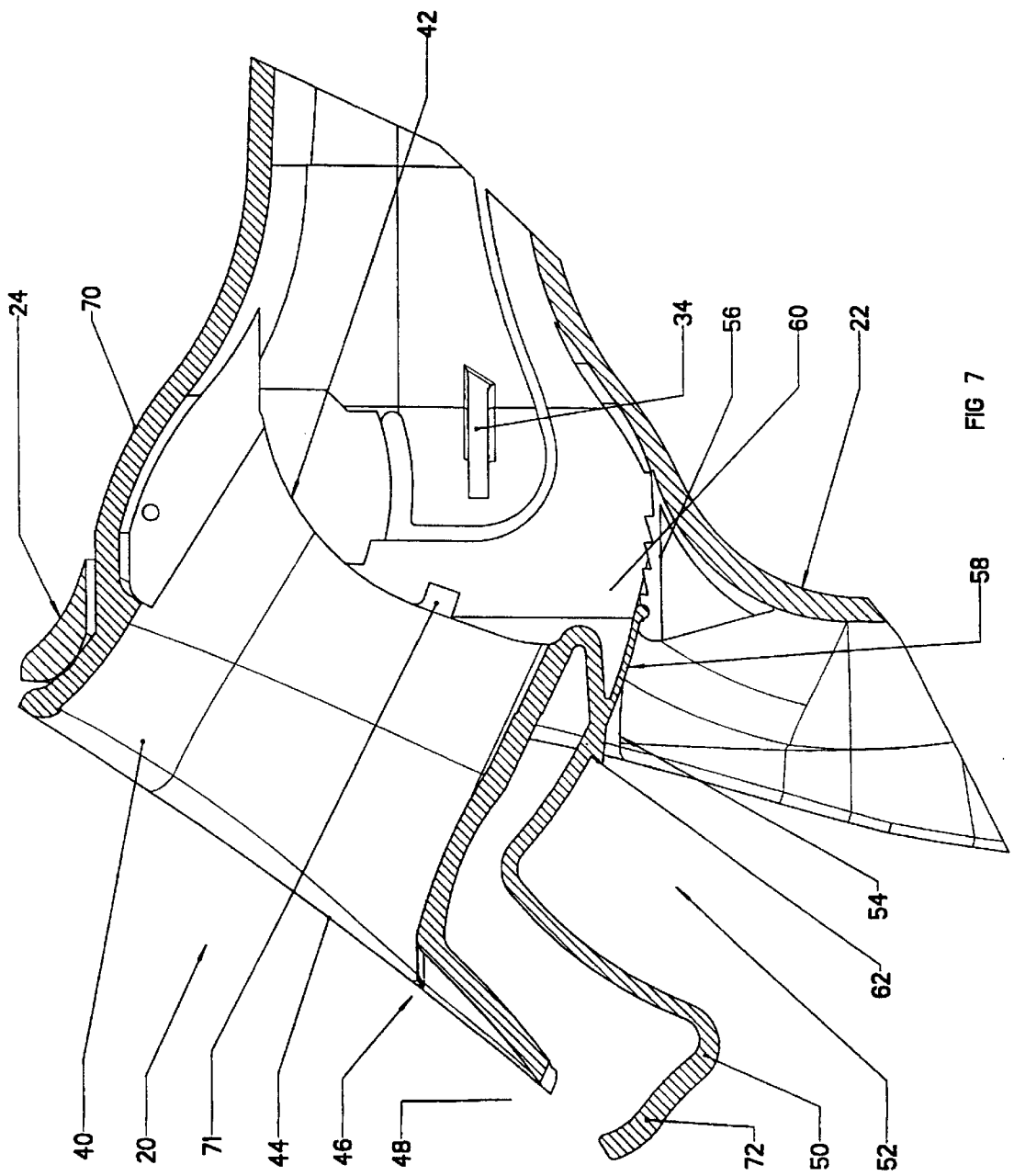
FIG. 7 is an enlarged sectional view of part of an actuator of the speculum shown in FIG. 6.

The actuator 20 is provided with an integral finger 70. The finger 70 extends from the forward edge 42 and is accommodated at its proximal end in the cut-out 30. The previously mentioned pins which are received in the detents 32 for pivotally coupling the actuator 20 to the main body 12, extend laterally from opposite sides of the proximal end of finger 70. The finger 70 is located between the upper longitudinal edges of fingers 14A and 14B, and is diametrically opposite the finger 28. The distal end of finger 70 together with the distal end of finger 28 form a duck bill like structure when the actuator 20 is in the free or closed state. In the embodiment shown, the distal end of the finger 28 extends beyond that of the finger 70. A locating lug 71 (see FIGS. 6 and 7) extends forward of edge 42 on opposite sides of the actuator 20 and sits slightly above the rib 34 when the edge 42 is received in the recess 36 of each rib 34.

The actuator 20 which includes the shell 40, thumb rest 46, mechanism 50, pawl 54, lugs 71 and finger 70 is made as a single integral component. Accordingly, the speculum 10 can be made from two separate components which can be easily and quickly constructed without the aid of any tools by pushing or otherwise locating the pins formed on the sides of the finger 70 into the detents 32.

In order to use the speculum 10, it is simply gripped by the handle 22 and slowly pushed into the cavity requiring dilation. With the thumb of the operator located in the thumb rest 46, the actuator 20 is pushed in the direction of insertion to cause the actuator 20 to pivot about the pins located in the detents 32. This pivoting motion results in the immediate pivoting of finger 70 so that its distal end moves away from the distal end of finger 28. While this occurs the barb 60 engages successive teeth on the rack 56 to provide tactile feedback of the motion of the finger 70. After a predetermined degree of pivoting of actuator 20, further pivoting results the barb 62 engaging the rack 56 and the forward edge 42 seating in recess 36 and bearing against the rib 34 on each of the fingers 14. As further thumb pressure is applied the actuator 20 continues to pivot which results in the fingers 14A and 14B moving about their respective hinges 26 so that their distal ends move away from each other. As the actuator 20 is pivoted, the second barb 62 engages successive teeth on the rack 56. At any time, if the thumb pressure is released once the barb 62 engages one of the teeth, the fingers 14, 70 and 28 are held in a fixed relationship to each other.

In order to allow the fingers to collapse and pivot back toward each other, the mechanism 50 is pushed upwardly and backwardly resulting in a lifting of the pawl 54 thereby disengaging the barb 62 from the rack 56.

It will be appreciated that when in use, the cavity being dilated can be visualised or instrumented through the shell 40 of the actuator 20 and ring like structure 24 of the main body 12. As the speculum 10 can be made from only two components and assembled in a matter of seconds without the aid of any tools, it can be manufactured at such a low cost that it can be used once and then disposed of. Further, the actuator 20 is only in abutment with the ends of fingers 14, therefore there is very little frictional engagement of the components of the speculum 10. This avoids the problem of the speculum "sticking open" due to high frictional forces when in use. This may occur for example with speculums in which an actuator pushes laterally against the inside surfaces of dilator fingers to cause them to spread. In the present speculum, the actuator only pushes against the proximal ends of the fingers. essentially in the direction of insertion of the speculum.

Now that an embodiment of this invention has been described in detail, it will be apparent to those skilled in the relevant arts that numerous modifications and variations may be made without departing from the basic inventive concepts. For example, the finger 28 is shown as being fixed to the main body 12 in a manner so that it does not pivot. However, it will be possible to construct the speculum 10 with the finger 28 supported by an integral hinge similar to hinges 26 so that it can be pivoted away from fingers 14 and 70. This will naturally require changes in the design of the actuator 20 so that it also abuts the distal end of the finger 28 to cause the pivoting motion. Further, the releasable locking mechanism 52 is not a critical part of the invention and can be dispensed with so that the fingers can be held apart by the maintaining of thumb pressure on the thumb rest 46.

The speculum 10 can also be provided with one or more stops to limit the pivoting motion of the actuator 20 and thus the degree of spread of the fingers 14, 28 and 70. In its simplest form this could be achieved by simply forming a stop bar or face on say the actuator 20 to come into contact with the main body 12 after a predetermined degree of pivoting with the actuator 20.

While the speculum 10 can be made from any material including stainless steel, it is preferred that it be made from a plastics material to facilitate low manufacturing cost and ease of construction.

All such modifications and variations are deemed to be within the scope of the present invention, the nature of which is to be determined from the foregoing description and the appended claims.

I claim:

1. A speculum for dilating a body cavity including:
   a main body;
   a plurality of first dilator fingers, coupled at their respective proximal ends to the main body in a manner to allow the respective distal ends of the first fingers to move away from each other; and,
   an actuator pivotally coupled to the main body, the actuator provided with a second finger fixed thereto, wherein the actuator can be pivoted into abutment with the proximal ends of the first dilator fingers causing the distal ends of the first fingers and the second finger move away from each other thereby dilating the body cavity.

2. A speculum according to claim 1 wherein the actuator is arranged to pivot through a first angle prior to abutment with the first fingers so that the distal end of the second finger commences to move before the distal ends of the first fingers move.

3. A speculum according to claim 2 wherein the main body is provided with a third fixed finger which is located between adjacent ones of the first fingers and opposite the second finger.

4. A speculum according to claim 3 wherein the distal ends of the second and third fingers extend beyond the distal ends of the first fingers.

5. A speculum according to claim 4 wherein respective distal ends of first fingers are located inside the second and third fingers when the speculum is in a fully closed state.

6. A speculum according to claim 3 wherein the first fingers are integrally formed with the main body and provided with respective integral hinges to allow movement away from each other.

7. A speculum according to claim 6 wherein each hinge has a hinge axis about which its corresponding finger can move, said hinge axis being canted so that the movement of the corresponding finger is a combined upward and sideways movement.

8. A speculum according to claim 3 wherein said main body comprises a first ring like structure to which said first dilator fingers are attached and said actuator comprises a second ring like structure which pivots inside said first ring like structure, said first and second ring like structures defining a window through which the cavity can be viewed when the distal ends of the fingers are moved away from each other.

9. A speculum according to claim 3 further comprising a releasable locking mechanism for locking the relative positions of the fingers, and subsequently releasing the fingers.

10. A speculum according to claim 9 wherein said mechanism comprises a first component provided on said actuator and a second component provided on said main body, said first and second components arranged to engage each other when said actuator is pushed in the direction of insertion, and adapted to release from each other when force is applied to said actuator in a direction oblique to the direction of insertion.

11. A speculum according to claim 10 wherein said first component comprises one of a pawl and a rack of teeth like projections, and the second component comprises the other of the pawl and the rack, said pawl and rack being biased into engagement when the actuator is pushed in the direction of insertion, and being lifted apart to effect disengagement when said force is applied.

12. A speculum for dilating a body cavity including:

a main body;

a plurality of first dilator fingers coupled at their respective proximal ends to main body in a manner to allow the respective distal ends of the first fingers to move away from each other; and an actuator pivotally coupled to the main body, the actuator provided with a second finger fixed thereto, the second finger located between adjacent ones of the first fingers, the actuator arranged to abut the proximal ends of the first fingers when pivoted in a first direction, whereby when the speculum is in a fully closed state and actuator is pivoted in a first direction a distal end of the second fingers initially pivots away from the first fingers and when the actuator abuts the first fingers it causes their distal ends to move away from each other thereby dilating the body cavity.

13. A speculum for dilating a body cavity including:

a main body;

a plurality of first dilator fingers hinged at their proximal ends to the main body about respective canted hinge axes to allow the first dilator fingers to move with a combined upward and sideways motion; and an actuator pivotally coupled to the main body, the actuator provided with a second finger fixed thereto so that the actuator can be pivoted into abutment with the first dilator fingers causing the first fingers to move outwardly with said combined upward and sideways motion and the second finger to move away from the first fingers thereby dilating the body cavity.

* * * * *

UNITED STATES PATENT AND TRADEMARK OFFICE
CERTIFICATE OF CORRECTION

PATENT NO.    : 6,174,282 B1                                          Page 1 of 1
DATED         : January 16, 2001
INVENTOR(S)   : Eric Gay Chee Tan It is certified that error appears in the above-identified patent and that said Letters Patent is hereby corrected as shown below:

<u>Title page,</u>
Item [75], Inventor, change "Gary Gay Chee Tan" to -- Eric Gay Chee Tan --

<u>Column 6,</u>
Line 41, after "second finger" insert -- to --

<u>Column 7,</u>
Line 30, after "proximal ends to" insert -- the --

Signed and Sealed this

Thirty-first Day of December, 2002

JAMES E. ROGAN
*Director of the United States Patent and Trademark Office*